United States Patent [19]

Rothschild et al.

[11] Patent Number: 5,374,526
[45] Date of Patent: Dec. 20, 1994

[54] METHOD FOR DETERMINING GENETIC MARKER FOR INCREASED PIG LITTER SIZE

[75] Inventors: Max E. Rothschild; Carol D. Jacobson, both of Ames, Iowa

[73] Assignee: Iowa State University Research Foundation, Inc., Ames, Iowa

[21] Appl. No.: 961,819

[22] Filed: Oct. 19, 1992

Related U.S. Application Data

[63] Continuation-in-part of Ser. No. 687,708, Apr. 19, 1991, abandoned.

[51] Int. Cl.$^5$ .................... C12Q 1/68; C12P 19/34; C07H 21/04; C07H 17/00
[52] U.S. Cl. ........................ 135/6; 435/91.1; 536/23.1; 536/24.3; 536/24.31; 536/24.33; 935/77; 935/78
[58] Field of Search .................. 435/6, 91.1; 536/18.7, 536/23.1, 24.3, 24.33, 23.1, 24.31; 935/77, 78

[56] References Cited

U.S. PATENT DOCUMENTS

| | | | |
|---|---|---|---|
| 4,582,788 | 4/1986 | Erlich | 435/6 |
| 4,666,828 | 5/1987 | Gusella | 435/6 |
| 4,742,000 | 5/1988 | Greene | 435/7 |
| 4,770,994 | 9/1988 | Rittenhouse | 435/7 |
| 4,772,549 | 9/1988 | Frossard | 435/6 |
| 4,861,708 | 8/1989 | Frossard | 435/6 |
| 5,041,371 | 8/1991 | Cowan et al. | 435/6 |

OTHER PUBLICATIONS

Entry 57681, *American Type Culture Collection Catalogue*, Sep. 1990, p. 82.
Green et al., *Nature* (London) 320:134–139 (1986).
Castagnoli et al., *Nucl. Acids Res.*, 15:886 (1987).
Coleman et al., *Nucl. Acids Res.*, 16:7208 (1988).
Lehrer et al., *The Lancet*, 335:622–624 (Mar. 17, 1990).
Koike et al., *Nucl. Acids Res.*, 15:2499–2513 (1987).
Koike et al., *Biochemistry*, 26:2563–2568 (1987).
Jung et al., *Theor. Appl. Genet.*, 77:271–274 (1989).
Hoganson et al., *Abstract for Annual Meeting of Midwestern Section of the American Society of Animal Science*, Mar. 26–28, 1990.
Jung et al., *Animal Genetics*, 20:79–91 (1989).
Flanagan et al., *Immunogenetics*, 27:465–469 (1988).
Kumar et al., *Cell*, 51:941–951 (1987).
Cowen et al., *Theor. Appl. Genet.*, 79:577–582 (1990).
Zaretsky et al., *FEBS Letters*, 265:46–50 (1990).
Rothschild et al., "Genetic Variability of the Swine Estrogen Receptor and Heat Shock Genes and Their Relationship to Reproduction and Health," *Abstract for Annual Meeting of American Society of Animal Science*, Aug. 6–9, 1991.
Rothschild et al., "PvuII Polymorphisms at the Porcine Oestrogen Receptor Locus," *Animal Genetics*, 22:448 (1991).
Rothschild et al., "Estrogen Receptor Gene Restriction Fragment Length Polymorphisms in U.S. Breeds of Swine," *Abstract for Annual Meeting of Midwestern Section of American Society of Animal Science and American Dairy Science Assn.*, Mar. 23–25, 1992.
Chardon et al., "Restriction Fragment Length Polymorphism of the Major Histocompatibility Complex of the Pig," *Immunogentics*, 21:161–171 (1985).

*Primary Examiner*—Margaret Parr
*Assistant Examiner*—Miguel Escallon
*Attorney, Agent, or Firm*—Zarley, McKee, Thomte, Voorhees & Sease

[57] ABSTRACT

Disclosed herein are genetic markers for pig litter size, methods for identifying such markers, and methods of screening pigs to determine those more likely to produce larger litters. The markers are based upon the presence or absence of certain polymorphisms in the pig estrogen receptor gene. Preferably, the polymorphism is a restriction fragment length polymorphism (RFLP). A 3.7 kilobase fragment and a 4.3 kilobase fragment obtained by digesting pig genomic DNA with the restriction endonuclease Pvu II and detecting the fragments with a probe comprising a detectably labeled human estrogen receptor gene are associated with increased litter size.

7 Claims, 2 Drawing Sheets

FIG. 1

GENE ARRANGEMENT (FROM ORIGINAL DATA)

ESR FRAGMENT (GENE)
4.3 kb Pvu

"BENEFICIAL LITTER SIZE GENE"

3.7 kb Pvu II
ESR FRAGMENT (GENE)

"REGULAR LITTER SIZE GENE"

GENE ARRANGEMENT (AFTER RECOMBINATION)
(FROM NEW DATA)

ESR FRAGMENT (GENE)
4.3 kb Pvu II

"REGULAR LITTER SIZE GENE"

3.7 kb Pvu II
ESR FRAGMENT (GENE)

"BENEFICIAL LITTER SIZE GENE"

FIG.2

METHOD FOR DETERMINING GENETIC MARKER FOR INCREASED PIG LITTER SIZE

This application is a continuation-in-part application of U.S. patent application Ser. No. 07/687,708, filed Apr. 19, 1991, now abandoned which is incorporated herein by reference in its entirety.

FIELD OF THE INVENTION

This invention relates generally to the detection of genetic differences for reproductive efficiency among pigs and particularly to genetic markers useful for identifying pigs more likely to produce larger litter sizes.

BACKGROUND OF THE INVENTION

Reproductive efficiency, which can be defined as the number of pigs produced per breeding female, is the major limiting factor in the efficient production of pork. The number of pigs born alive in the United States averages approximately 9.5 pigs per litter. Heritability for litter size is low (10% -15%), and standard genetic methods of selecting breeding females on the basis of past litter size have not been effective. Therefore, there is a need for an approach that deals with selection for reproduction at the cellular or DNA level.

Chinese breeds are known for reaching puberty at an early age and for their large litter size. American breeds are known for their greater growth rates and leanness. Thus, it would be desirable to combine the best characteristics of both types of breeds, thereby improving the efficiency of U.S. pork production. These efforts would be greatly assisted by the discovery of genes or genetic markers that are associated with increased litter size in pigs.

Reproduction in mammals takes place in response to a chain of events that occur between the brain and the reproductive organs. The steroid hormones, such as estrogen, play a crucial role. Steroid hormones interact with cells and tissues, initiating a series of events that result in the ability to reproduce successfully.

In pigs, estrogen, which is produced mainly by the ovaries, has profound effects on the uterus, brain, and pituitary gland. Estrogens modulate the onset of puberty, reproductive behaviors, cyclic release of gonadotropins, and feeding behavior. The effects of estrogens take place as a result of the binding of estrogen to specific receptor proteins found in the nucleus of the estrogen-responsive cells. McEwen, et al., *Recent Prog. Horm. Res.*, 38:41-92 (1982), incorporated herein by reference.

The gene responsible for coding for the human estrogen receptor has been identified, and it is publicly available from the American Type Culture Collection. See ATCC Catalog Sept. 1990, page 112, entry 57681, incorporated herein by reference. The probe is named pOR3 and is 1.3 kb. Green et al., *Nature* (London) 320:134-139 (1986), incorporated herein by reference. The human gene is known to be polymorphic as a result of restriction fragment length polymorphism (RFLP) analysis. Castagnoli et al., *Nucl. Acids Res.*, 15:886 (1987) and Coleman et al., *Nucl. Acids Res.*, 16:7208 (1988), both of which are incorporated herein by reference. The functional differences relating to these different genotypes are not well understood, but they have been implicated in increased spontaneous abortions in humans with breast cancer. Lehrer et al., *The Lancet*, 335:622-624 (Mar. 17, 1990), incorporated herein by reference.

The estrogen receptor gene has been isolated and sequenced for other species, but not for pigs. Koike et al., *Nucl. Acids Res.*, 15:2499-2513 (1987), incorporated herein by reference, reports the isolation and sequencing of a cDNA clone of the rat uterus estrogen receptor. The authors state that a comparison of rat, human, and chicken estrogen receptor sequences indicates the presence of three highly conserved regions, suggesting that these regions play important roles in estrogen receptor function.

In addition, Koike et al. *Biochemistry* 26:2563-2568 (1987), incorporated herein by reference, reports the partial characterization of the porcine estrogen receptor binding site. The paper reports a fragment of about 30 kDa that probably corresponds to the hydrophobic C-terminal-half region and has a greater than 90% homology with the corresponding rat, human, and chicken sequences.

RFLP analysis has been used by several groups to study pig DNA. Jung et al., *Theor. Appl. Genet.*, 77:271-274 (1989), incorporated herein by reference, discloses the use of RFLP techniques to show genetic variability between two pig breeds. Polymorphism was demonstrated for swine leucocyte antigen (SLA) Class I genes in these breeds. Hoganson et al., *Abstract for Annual Meeting of Midwestern Section of the American Society of Animal Science*, Mar. 26-28, 1990, incorporated herein by reference, reports on the polymorphism of swine major histocompatibility complex (MHC) genes for Chinese pigs, also demonstrated by RFLP analysis. Jung et al. *Animal Genetics*, 20:79-91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

Prior to the present invention, RFLP analysis has not been applied to the pig estrogen receptor gene, which has not even been isolated or characterized. The present invention overcomes these deficiencies. It provides genetic markers, based upon the discovery of polymorphisms in the pig estrogen receptor gene, which relate to increased litter size in pigs. This will permit genetic typing of pigs for their estrogen receptor genes and determining the relationship of specific RFLPs to increased litter size. It will also permit the identification of individual males and females that would be expected to produce a litter size larger than the average for their breed. Thus, the markers will be selection tools in breeding programs to develop lines and breeds that produce litters containing a larger number of offspring.

SUMMARY OF THE INVENTION

It is an object of the invention to provide a method of screening pigs to determine those more likely to produce larger litters.

Another object of the invention is to provide a method for identifying genetic markers for pig litter size.

A further object of the invention is to provide genetic markers for pig litter size.

Yet another object of the invention is to provide a kit for evaluating a sample of pig DNA for specific genetic markers of litter size.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides a method for screening pigs to determine those more likely to produce a larger litter when bred. A sample of genomic DNA is obtained from a pig, and the sample is analyzed to determine the presence or absence of a polymorphism in the estrogen receptor gene that is correlated with increased litter size. Preferably, the polymorphism is a restriction fragment length polymorphism.

The presence or absence of a specific fragment or RFLP pattern is determined by the following steps. First, the genomic DNA is digested with a restriction endonuclease that cleaves the pig estrogen receptor gene in at least one place. Second, the fragments obtained from the digestion are separated, preferably by gel electrophoresis. Third, the fragments are detected with a probe capable of hybridizing to them. This generates a RFLP pattern. Finally, the RFLP pattern is compared to a known RFLP pattern for this gene that is correlated with increased litter size. The second pattern is a control pattern and is obtained by using the same restriction endonuclease and the same probe or an equivalent probe. Preferably, the probe is the human estrogen receptor gene.

In another embodiment, the invention comprises a method for identifying a genetic marker for pig litter size. Male and female pigs of the same breed or breed cross or similar genetic lineage are bred, and the number of offspring produced by each female pig is determined. The polymorphism in the estrogen receptor gene of each pig is determined and associated with the number of offspring. Preferably, RFLP analysis is used to determine the polymorphism, and most preferably, the genomic DNA is digested with the restriction endonuclease Pvu II. For pigs of the Meishan breed, such analysis produces allelic 3.7 and 4.3 kilobase fragments associated with increased litter size.

The invention further comprises a kit for evaluating a sample of pig DNA. At a minimum, the kit is a container with one or more reagents that identify polymorphism in the pig estrogen receptor gene. Preferably, the reagent is a probe that hybridizes with the pig estrogen receptor gene or fragments thereof. Preferably, the probe is the human estrogen receptor gene. Preferably, the kit further contains a restriction enzyme that cleaves the pig estrogen receptor gene in at least one place.

The accompanying figures, which are incorporated in and constitutes a part of this specification, illustrate one embodiment of the invention and, together with the description, serve to explain the principles of the invention.

DETAILED DESCRIPTION OF THE INVENTION

Reference will now be made in detail to the presently preferred embodiments of the invention, which, together with the following examples, serve to explain the principles of the invention.

The invention relates to genetic markers for litter size in pigs. It provides a method of screening pigs to determine those more likely to produce a larger litter when bred by identifying the presence or absence of a polymorphism in the estrogen receptor gene that is correlated with increased litter size. As used herein, the term "increased litter size" means a significant increase in litter size above the mean of a given population. Thus, the invention relates to genetic markers and methods of identifying those markers in a female pig of a particular breed, strain, population, or group, whereby the female pig is more likely to produce a litter that is significantly increased in size (number) above the mean litter size for that particular breed, strain, population, or group.

The use of RFLPs is the preferred method of detecting the polymorphism. However, since the use of RFLP analysis depends ultimately on polymorphisms and DNA restriction sites along the nucleic acid molecule, other methods of detecting the polymorphism can also be used. Such methods include ones that analyze the polymorphic gene product and detect polymorphisms by detecting the resulting differences in the gene product.

RFLP analysis in general is a technique well-known to those skilled in the art. See, for example, U.S. Pat. Nos. 4,582,788 issued Apr. 15, 1986 to Erlich and 4,666,828 issued May 19, 1987 to Gusella, 4,772,549 issued Sep. 20, 1988 to Frossard, and 4,861,708 issued Aug. 29, 1989 to Frossard, all of which are incorporated herein by reference. Broadly speaking, the technique involves obtaining the DNA to be studied, digesting the DNA with restriction endonucleases, separating the resulting fragments, and detecting the fragments of various genes.

In the present invention, a sample of genomic DNA is obtained from a pig. Generally, peripheral blood cells are used as the source of the DNA. A sufficient amount of cells are obtained to provide a sufficient amount of DNA for analysis. This amount will be known or readily determinable by those skilled in the art. The DNA is isolated from the blood cells by techniques known to those skilled in the art.

In certain instances, it may be desirable to amplify the amount of DNA through the use of standard techniques, such as the polymerase chain reaction. This technique is described in U.S. Pat. Nos. 4,683,195, issued Jul. 28, 1987 to Mullis et al., 4,683,202, issued Jul. 28, 1987 to Mullis, 4,800,159 issued Jan. 24, 1989 to Mullis, et al., 4,889,818 issued Dec. 26, 1989 to Gelfand, et al., and 4,902,624 issued Feb. 20, 1990 to Columbus, et al., all of which are incorporated herein by reference.

The isolated DNA is then digested with a restriction endonuclease that cleaves or cuts DNA hydrolytically at a specific nucleotide sequence, called a restriction site. Such endonucleases, also called restriction enzymes, are well-known to those skilled in the art. For the present invention, one should be chosen that cleaves the pig estrogen receptor gene in at least one place, producing at least two fragments of the gene. A determination is made as to whether or not any such fragments are polymorphic and if any polymorphism (RFLP) is associated with litter size by techniques known in the art in conjunction with the teachings contained herein. Preferably, such restriction endonuclease is Pvu II. The amount of such enzyme to be added to the sample containing the pig DNA and the other appropriate conditions for treating the sample will be readily determinable to persons skilled in the art, given the teachings contained herein.

The restriction fragments are then analyzed by known techniques that generally involve either the separation of the fragments and subsequent blotting and hybridization to obtain a particular pattern or the determination of different sizes of the fragments. The latter permits the identification of one or more fragments (markers) for increased litter size. The preferred technique is gel electrophoresis.

In this technique, the digested fragments are separated in a supporting medium by size under the influence of an applied electric field. Gel sheets or slabs, such as agarose or agarose-acrylamide, are typically used as the supporting medium. The sample, which contains the restriction fragments, is added to one end of the gel. One or more size markers are run on the same gel as controls to permit an estimation of the size of the restriction fragments. This procedure generally permits a degree of resolution that separates fragments that differ in size from one another by as little as 100 base pairs.

The separated fragments preferably are then denatured and transferred physically from the gel onto a filter, preferably a nylon membrane, by contacting the gel with the filter in the presence of appropriate reagents and under appropriate conditions that promote the transfer of the DNA. Such reagents and conditions are well-known to those skilled in the art. Thus, the relative positions of the DNA fragments resulting from the separation procedure are maintained.

The next step involves the detection of the various categories of sizes of the fragments or, alternatively, the detection of a fragment of a particular size. The latter may be of particular interest because it is a genetic marker associated with increased litter size. In either case, the preferred technique is the use of a hybridization probe. Such a probe is an oligonucleotide or polynucleotide that is sufficiently complimentary or homologous to the fragments to hybridize with them, forming probe-fragment complexes. Preferably, the probe is a cDNA probe. The oligonucleotide or polynucleotide is labeled with a detectable entity. This permits the detection of the restriction fragments, to which the probes are hybridized. The probes are labeled by standard labeling techniques, such as with a radiolabel, enzyme label, fluorescent label, biotin-avidin label, and the like. See U.S. Pat. Nos. 4,711,955 issued Dec. 8, 1987 to Ward et al. and 4,868,103 issued Sep. 19, 1989 to Stavrianopoulos et al., both of which are incorporated herein by reference.

In the present invention, a cDNA for the human estrogen receptor gene is used as the probe. The probe is labeled with a detectable moiety. Preferably, the detectable moiety is $^{32}P$ or biotin-avidin. The inventors have discovered that this probe is sufficiently homologous to the pig estrogen receptor gene to bind to it and to the various fragments produced by restriction endonucleases. However, other substantially equivalent probes can be determined by those skilled in the art, given the teachings contained herein. As used herein, a probe that is "substantially equivalent" to the human estrogen receptor gene probe is one that hybridizes to the same polymorphic fragments of digests of the pig estrogen receptor gene as does the human estrogen receptor gene probe when the same restriction enzyme is used under the same conditions. For example, particular fragments that are associated with pig litter size can be sequenced by known techniques, and synthetic probes can be prepared, also by known techniques. Alternatively, the pig estrogen receptor gene, once cloned, may be used for a probe.

In the preferred method, the probes are contacted with the nylon membrane that contains the restriction fragments for a sufficient period of time and under appropriate hybridizing conditions for the probes to hybridize to the fragments. The filter is then preferably washed to remove unbound probes and other unwanted materials.

The probe-fragment complexes, which are bound to the filter, are then detected by known techniques. For example, if the probe has been radioactively labeled ($^{32}P$), detection involves contacting the nylon membrane paper with a piece of radiosensitive film. Following an appropriate exposure period, the fragments of interest, including control fragments, are visualized.

The detection step provides a pattern, resulting from the separation of the fragments by size. Comparison of these fragments with control fragments of known size that have also been run on the same gel permits the estimation of the size of the various groups of fragments. The various polymorphisms in the pig estrogen receptor gene are then determined by comparison of the patterns produced by similar analysis of DNA from a number of different pigs. For some of the individual pigs, the patterns will differ from the usual pattern produced by most of the other pigs. This will be due to one or more restriction fragment length polymorphisms, i.e., restriction fragments of a different length produced by the endonuclease that cuts the pig estrogen receptor gene. This indicates different base pair sequences in such pigs.

Once a particular RFLP has been identified, i.e., a restriction fragment of a particular length, a probe to this fragment may be constructed by the use of known techniques. This permits alternative and faster formats for detecting such polymorphism. For example, once the DNA is digested, a sandwich hybridization format can be used. Such an assay is disclosed in U.S. Pat. Nos. 4,486,539 issued Dec. 4, 1984 to Ranki, et al., and 4,563,419 issued Jan. 7, 1986 to Ranki, et al., both of which are incorporated herein by reference. The sample is brought into contact with a capture probe that is immobilized on a solid carrier. The probe binds the fragment. The carrier is then washed, and a labeled detection probe is added. After additional washing, the detection probe is detected, thereby demonstrating the presence of the desired fragment.

Once the RFLP pattern has been determined or a particular polymorphic fragment has been determined, it is compared to a second, known RFLP pattern or fragment that is correlated with increased litter size. This second pattern or fragment has also been determined from the pig estrogen receptor gene, using the same restriction endonuclease as the first and the same probe or an equivalent thereof under the same conditions.

In an alternative embodiment of the invention, the restriction fragments can be detected by solution hybridization. In this technique, the fragments are first hybridized with the probe and then separated. The separated probe-fragment complexes are then detected by detecting the detectable moiety in the probe as discussed above. Generally, such complexes are detected on the gel without transfer to filter paper.

Although the above methods are described in terms of the use of a single restriction enzyme and a single probe, the methods are not so limited. One or more additional restriction enzymes and/or probes can be used, if desired. Additional enzymes and constructed probes can be determined through routine experimentation.

Genetic markers for pig litter size are determined as follows. Male and female pigs of the same breed or breed cross or derived from similar genetic lineages are mated. The number of offspring produced by each female pig is determined. RFLP analysis of the parental DNA is conducted as discussed above in order to determine polymorphisms in the estrogen receptor gene of each pig. The polymorphisms are associated with the number of offspring. At least 20 and preferably at least 40 female pigs are used in making these determinations. The number of times each female produces a litter (i.e., the parity) is at least 1 time. Preferably, the cycle of breeding and giving birth is repeated at least 2 times and most preferably 3 times. The preferred breeds of pigs are Meishan, Fengjing, Minzhu, Duroc, Hampshire, Landrace, Large White, Yorkshire, Spotted Poland China, Berkshire, Poland China, and Chester White. The most preferred breeds are Duroc, Hampshire, Landrace, Large White, Yorkshire, and Chester White.

When this analysis is conducted for the Meishan breed and the polymorphism is determined by RFLP analysis using the restriction endonuclease Pvu II, polymorphic fragments of approximately 7.7 kilobase, 5.0 kilobase, 4.3 kilobase, and 3.7 kilobase were identified. The 4.3 kb and 3.7 kb fragments were shown to be alleles, and both were shown to be associated with increased litter size. This allelic pair is also believed to be associated with increased litter size in American breeds. This outcome is similar to the situation disclosed in U.S. Pat. No. 4,666,828, previously referenced herein, where the inventor found two allelic markers for Huntington's disease, one marker in one family and the other in a second family.

Figure 1:
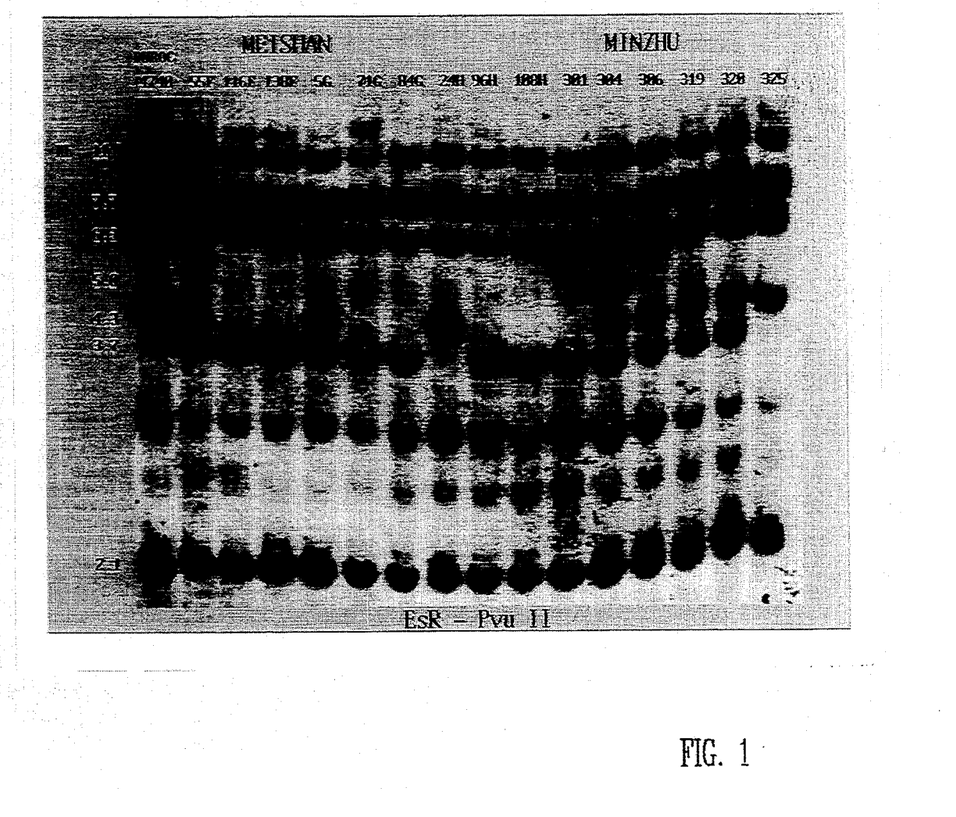
FIG. 1 shows RFLP analysis of Duroc (lane 1) and Chinese (lanes 2-16) pig DNA using the human estrogen receptor gene probe.
Figure 2:
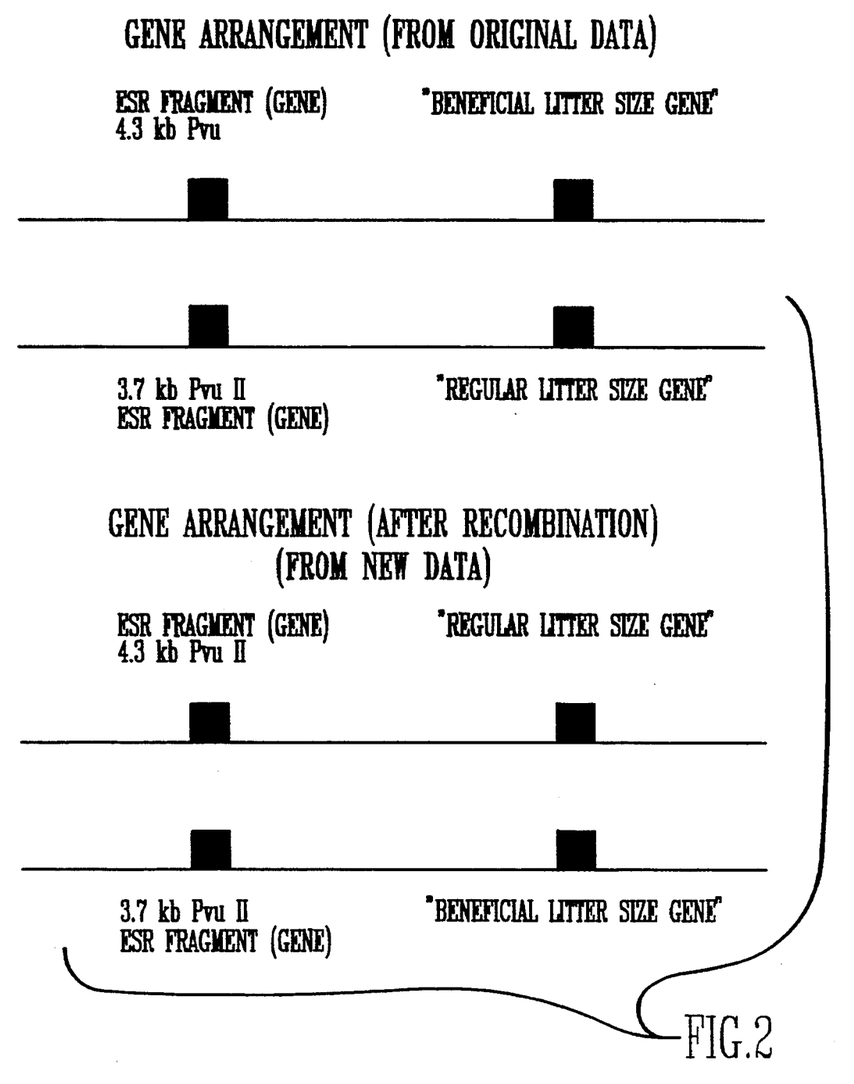
FIG. 2 shows the proposed outcome from recombination of the estrogen receptor gene (ESR) fragments and the beneficial litter size gene in two different Meishan herds.

Without wishing to be bound by theory, the inventors believe that the pig estrogen receptor gene is closely linked to a gene that influences litter size. In certain types of pigs, this gene provides for increased litter size. Therefore, the inventors call this gene the "beneficial litter size gene." Other types of pigs, which do not show increased litter size, carry what the inventors call the "regular litter size gene." The inventors also believe that, in the case of the 3.7 kb and 4.3 kb Pvu II ESR fragments, one of the fragments was originally linked to the regular litter size gene and the other was linked to the beneficial litter size gene. A recombination event rearranged the linkage, thus providing the situation where either the 3.7 kb fragment or the 4.3 kb fragment is a marker for increased litter size, depending upon the line or population being examined. See FIG. 2.

The reagents suitable for applying the methods of the invention may be packaged into convenient kits. The kits provide the necessary materials, packaged into suitable containers. Preferably, the containers are also supports useful in performing the assay. At a minimum, the kit contains a reagent that identifies a polymorphism in the pig estrogen receptor gene that is associated with an increased litter size. Preferably, the reagent is a probe that hybridizes with the pig estrogen receptor gene or fragments thereof. Preferably, both the probe and a restriction enzyme that cleaves the pig estrogen receptor gene in at least one place are included in the kit. In a particularly preferred embodiment of the invention, the probe comprises the human estrogen receptor gene, a pig estrogen receptor gene, or a gene fragment that has been labelled with a detectable entity and the restriction enzyme comprises Pvu II. Preferably, the kit further comprises additional means, such as reagents, for detecting or measuring the detectable entity or providing a control. Other reagents used for hybridization, prehybridization, DNA extraction, etc. may also be included, if desired.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the estrogen receptor gene is present. Preferably, RFLP analysis is performed with respect to the pig estrogen receptor gene, and the results are compared with a control. The control is the result of a RFLP analysis of the pig estrogen receptor gene of a different pig where the polymorphism of the pig estrogen receptor gene is known. Similarly, the estrogen receptor genotype of a pig may be determined by obtaining a sample of its genomic DNA, conducting RFLP analysis of the estrogen receptor gene in the DNA, and comparing the results with a control. Again, the control is the result of RFLP analysis of the estrogen receptor gene of a different pig. The results genetically type the pig by specifying the polymorphism in its estrogen receptor genes. Finally, genetic differences among pigs can be detected by obtaining samples of the genomic DNA from at least two pigs, identifying the presence or absence of a polymorphism in the estrogen receptor gene, and comparing the results.

These assays are useful for identifying genetic markers relating to litter size, as discussed above, for identifying other polymorphisms in the estrogen receptor gene that may be correlated with other characteristics, and for the general scientific analysis of pig genotypes and phenotypes.

The genetic markers, methods, and kits of the invention are also useful in a breeding program to improve litter size in a breed, line, or population of pigs. Continuous selection and breeding of sows that are at least heterozygous and preferably homozygous for a polymorphism associated with increased litter size would lead to a breed, line, or population having higher numbers of offspring in its litters. Thus, the markers are selection tools.

It is to be understood that the application of the teachings of the present invention to a specific problem or environment will be within the capabilities of one having ordinary skill in the art in light of the teachings contained herein. The examples of the products and processes of the present invention appear in the following examples.

EXAMPLE 1

Genetic Marker for Increased Litter Size in Meishan Pigs

Materials and Methods

The procedures for detecting the restriction fragment length polymorphisms (RFLPs) were as follows. Ten ml of sterile blood were obtained from each pig. Isolation of genomic DNA was then performed from white blood cells, followed by digestion with Pvu II restriction endonuclease, Southern blotting, and hybridization with the estrogen receptor gene probe as outlined in Flanagan et al., Immunogenetics 27:465–469 (1988), incorporated herein by reference. Molecular sizes of the restriction fragments were determined by comparison with molecular size markers for Hind III cut lambda DNA restriction fragments run in parallel on the separation gels. The estrogen receptor probe was a 1.3 kb cDNA fragment from the estrogen receptor gene isolated from humans (locus ESR) that was obtained from The American Type Culture Collection NIH Repository of Human and Mouse DNA Probes (ATCC No. 57680 or 57681 both of which are incorporated herein by reference). The cDNA was excised as a 1.3 kb EcoRI insert according to the method of Green et al., Nature 320:134–139 (1986), incorporated herein by reference. About 100 ng of the isolated fragment was random primer labeled with $^{32}P$.

Results

Using the human estrogen receptor gene as a probe, we have used RFLP analysis on Chinese, American, and NIH miniature pigs to detect genetic differences for the homologous estrogen receptor locus in the pig. Our results reveal that there are at least four fragments that are polymorphic in the pig. These fragments are at 3.7, 4.3, 5.0, and 7.7 kb.

Further, we investigated whether the polymorphic restriction fragment patterns were related to litter size in our original 22 Meishan females. See Table 1. Based on our results, having the 4.3 kb fragment seems to increase the litter size, while not having the 4.3 kb seems to be a disadvantage. These data indicate that we have found a gene marker for litter size in Meishan pigs.

TABLE 1

Means and standard errors of litter size in Meishan females by parity and estrogen receptor fragment.

| Fragments | | Parity 1 | Parity 2 | Parity 3 |
|---|---|---|---|---|
| With | NB | 12.7 ± .84 | 14.2 ± 1.16 | 16.3 ± .33 |
| 4.3 kb | NBA | 12.4 ± .81 | 12.8 ± .92 | 15.0 ± 1.53 |
| | N | 7 | 5 | 3 |
| Without | NB | 11.4 ± .71 | 11.4 ± 1.31 | 13.5 ± 1.84 |
| 4.3 kb | NBA | 10.9 ± .65 | 10.2 ± 1.17 | 13.3 ± 1.79 |
| | N | 14 | 11 | 4 |

NB = Number Born, NBA = Number Born Alive, N = Number of females having a first, second, or third parity record that have or do not have the 4.3 kb fragment

EXAMPLE 2

Pvu II and Pst Polymorphisms at the Estrogen Receptor Gene (ESR) Locus

Introduction

The extent of genetic variability at the ESR locus in pigs was generally unknown and the allelic nature of the DNA restriction fragments was undetermined. To determine the level of genetic variability and the allelism of the estrogen receptor gene (ESR), family data and a sample of a number of breeds was examined.

Materials and Methods

A population sample of 149 pigs, from the Iowa State University animal breeding farm near Madrid, Iowa, consisting of 10 Chester White (CW), 24 Duroc (D), 8 Fengjing (Fe), 12 Hampshire (H), 12 Landrace (L), 31 Meishan (Me), 6 Minzhu (Mz), 23 National Institutes of Health Miniature pigs (NIH MP), 10 Porcine Stress Syndrome (PSS) and 13 Yorkshire (Y) animals were used. The Durocs were subdivided into an outbred (DO) and an inbred population (DI). The PSS pigs are primarily of Yorkshire descent, but have some Pietran, Spotted and Poland China genetic background. In addition, 7 families, with a total of 26 living offspring, were studied. The breeds and strains contained both related and unrelated animals, and all pigs were raised according to approved animal care guidelines.

Ten to fifteen micrograms of genomic DNA (isolated from white blood cells) was digested with restriction enzymes Pvu II and Pst I, separated in 0.8% (Pvu II) or 0.7% (Pst I) agarose gels along with molecular weight standards, and Southern blotted to nylon membranes. The probe pOR3 was a 1.3 kb cDNA fragment of the human estrogen receptor gene (ESR locus) cloned into the vector pBR322. It was obtained from the American Type Culture Collection NIH Repository of Human and Mouse DNA Probes (ATCC No. 57680 (freeze dried E. coli containing the plasmid) or 57681 (purified DNA) both of which are incorporated herein by reference). The cDNA was excised as a 1.3 kb EcoRI insert from plasmid pOR3 and purified from agarose following electrophoresis according to the method of Green et al., "Human Estrogen Receptor cDNA Sequence, Expression, and Homology to V-erb-A," Nature 320:134–9 (1986), incorporated herein by reference. Approximately 100 ng of the isolated fragment was random primer labeled with $^{32}P$. Hybridizations were performed (modified from Rothschild et al., "Pvu II Polymorphisms at the Porcine Oestrogen Receptor Locus (ESR)," Animal Genetics 22:448 (1991), incorporated herein by reference) at +65° C. (0.5 M NaCl, 50 mM Sodium Phosphate pH 6.5, 5× Denhardt's solution, .2% SDS, 10% dextran sulfate) overnight. The membranes were washed twice at 25° C. in 2× SSC, 0.2% SDS and for 25 min at +65° C. in 0.7× SSC, 0.5% SDS. If needed, a more stringent wash was used (+68° C., 0.7× SSC, 0.5% SDS, 10–15 min). Membranes were exposed to film at −80° C. with intensifying screens for 1–4 days and the films photographically developed and evaluated.

Results and Discussion

Seven DNA fragments, of which four were polymorphic, were detected using the Pvu II restriction enzyme (Table 2) and the human ESR probe. The 11.0 kb, 6.3 kb and 2.1 kb fragments were seen in all animals while the 7.7 kb, 5.0 kb, 4.3 kb and 3.7 kb fragments were polymorphic in some of the breeds (Table 2).

The allelism of the Pvu II polymorphic fragments was determined in two ways. In the Meishan breed, it was noticed that the 4.3 kb and the 3.7 kb fragments appeared to segregate among sib groups. RFLP data were collected on living individuals resulting from matings involving Chinese pigs (families 1–3) and families of 4–7 of NIH minipigs (Table 3). Results in Table 3 demonstrate that the 4.3 kb and the 3.7 kb fragments are allelic, since in cases involving matings with a heterozygous individual, half the offspring received each allele.

In cases of homozygous matings, only the parental genotype was seen in the offspring. Further examination of additional sib groups and hybridization intensities also confirmed these results. Second, it was noticed that when the 5.0 kb fragment was present, the 7.7 kb fragment had a lighter hybridization signal. Further examination of blots where the 5.0 kb fragment was present verified this result. These results indicate that the 5.0 kb and the 7.7 kb fragments are allelic. The 5.0 kb and the 7.7 kb fragments segregated independently of the 4.3 kb and 3.7 kb fragments.

Eight DNA fragments were seen with the Pst I restriction enzyme of which the 15.5 kb, 5.2 kb, and the 2.5 kb fragments were non-polymorphic. Only the 10.0 kb, 9.6 kb, 9.2 kb, and the 7.8 kb fragments were polymorphic (Table 2). Occasionally a 13.5 kb fragment was also seen. For the families studied, the data was not informative enough to determine which Pst I fragments were allelic.

Summary

Pigs from a population consisting of eight U.S. breeds or strains and three Chinese breeds were examined by restriction fragment length polymorphism (RFLP) analysis of the estrogen receptor gene (ESR). Polymorphisms with Pst I and Pvu II restriction enzymes were observed, and the allelic nature of the Pvu II fragments could be deduced.

nature of the Pvu II fragments, and the association of the estrogen receptor gene (ESR) with higher litter size in the pig. This example provides additional data from a larger sample size. The data was collected with the cooperation of the Pig Improvement Company from three of their lines with the goal of demonstrating the extent of ESR association with higher litter size.

Materials and Methods

To further study this genetic variability at the ESR locus, a total of 175 pigs from three lines of pigs from the Pig Improvement Company (PIC) research herds were used. These analyses include 21 first litter sows from the PIC Line 92 (Chinese Meishan pigs), 105 multiparous sows from the PIC Line 94 (a cross of 50% Meishan and 50% from a PIC American line of pigs), and 62 multiparous sows (49 with litter data) from the Line 02 (consisting of primarily European Landrace pigs). The Line 92 (Meishan) was used since it represented an independent sample to the work shown in Example 1, and the Line 94 (a Meishan cross) was used because it represented a source of genetic material for a synthetic commercial line. In addition, Line 02 pigs were initially sampled because they represented one of the popular mothering breeds in the U.S. This line had undergone selection at PIC for prolificacy. These PIC pigs were used in an attempt to obtain data that would be subject to limited environmental influences so as to

TABLE 2

Frequency of polymorphic Pvu II and Pst I fragments in U.S. and Chinese swine breeds

| Breed | No. of Animals | Polymorphic Fragments (kb) | | | | | | | |
|---|---|---|---|---|---|---|---|---|---|
| | | Pvu II | | | | Pst I | | | |
| | | 7.7 | 5.0 | 4.3 | 3.7 | 10.0 | 9.6 | 9.2 | 7.8 |
| Chester White** | 10 | 100% | 30% | 100% | 10% | 43% | 86% | 14% | 100% |
| Yorkshire | 13 | 100% | 0% | 38% | 92% | — | — | — | — |
| Landrace** | 12 | 100% | 8% | 100% | 0% | 100% | 50% | 0% | 100% |
| Hampshire | 12 | 100% | 0% | 100% | 0% | 0% | 100% | 17% | 100% |
| Duroc-outbred | 12 | 100% | 0% | 100% | 0% | 0% | 100% | 67% | 92% |
| Duroc-inbred | 12 | 100% | 0% | 100% | 0% | 0% | 100% | 50% | 83% |
| Stress line | 10 | 100% | 0% | 90% | 70% | — | — | — | — |
| Meishan | 31 | 100% | 0% | 42% | 87% | — | — | — | — |
| Fengjing | 8 | 100% | 0% | 63% | 100% | — | — | — | — |
| Minzhu | 6 | 100% | 17% | 83% | 83% | — | — | — | — |
| NIH Miniature | 23 | 83% | 52% | 100% | 0% | — | — | — | — |

**For Pst I, 7 Chester White and 4 Landrace only

TABLE 3

Examples of family data and segregation of the 4.3 and 3.7 kb Pvu II fragments.

| Family | Sire Genotype | Dam Genotype | Offspring Genotypes |
|---|---|---|---|
| 1 | 4.3 kb/3.7 kb | 3.7 kb | 3 offspring - 4.3 kb/3.7 kb |
| | | | 1 offspring - 3.7 kb |
| 2 | 4.3 kb/3.7 kb | 4.3 kb | 6 offspring - 4.3 kb |
| | | | 4 offspring - 4.3 kb/3.7 kb |
| 3 | 3.7 kb | 3.7 kb | 7 offspring - 3.7 kb |
| 4 | 4.3 kb | 4.3 kb | 1 offspring - 4.3 kb |
| 5 | 4.3 kb | 4.3 kb | 1 offspring - 4.3 kb |
| 6 | 4.3 kb | 4.3 kb | 1 offspring - 4.3 kb |
| 7 | 4.3 kb | 4.3 kb | 2 offspring - 4.3 kb |

Only available living animals were typed.

EXAMPLE 3

Relationship of Pvu II and Pst Polymorphisms at the Estrogen Receptor Gene (ESR) Locus to Litter Size in Chinese and American Breeds and Their Crosses Introduction Examples 1 and 2 show the genetic variability at the estrogen receptor gene (ESR) locus in pigs, the allelic more clearly examine genetic effects on litter size. The total number of animals and litters surveyed is presented in Table 4.

Ten to fifteen micrograms of genomic DNA (isolated from white blood cells) was digested with restriction enzymes Pvu II or Pst I, separated in 0.8% (Pvu II) or 0.7% (Pst I) agarose gels along with molecular weight standards, and Southern blotted to nylon membranes. The probe was prepared as in Example 2. Hybridizations were performed (modified from Rothschild et al. 1991) at +65° C. (0.5M NaCl, 50 mM Sodium Phosphate pH 6.5, 5× Denhardt's solution, 0.2% SDS, 10% dextran sulfate) overnight. The membranes were washed twice at 25° C. in 2× SSC, 0.2% SDS and for 25 min at +65° C. in 0.7× SSC, 0.5% SDS. If needed, a more stringent wash was used (+68° C., 0.7× SSC, 0.5% SDS, 10–15 min). Membranes were exposed to film at −80° C. with intensifying screens for 1–4 days and the films photographically developed and evaluated.

Analysis of the data occurred using two statistical methods. The first is a method called the animal mixed model method. See Kennedy et al. 1992 incorporated herein by reference. It uses a model to describe the data that includes typical environmental effects, the genetic relationships between animals, and the effect of the fragments or fragment genotypes. The second method is more widely used and is called the least squares analysis method. The model using the least squares method included the usual environmental effects, the effects of the sire and dam of the sows whose litter records were being used, and also the effect of the fragments or fragment genotypes. Kennedy et al. (1992) has suggested that use of the animal model is preferred because it reduces the probability of incorrectly declaring significant differences for effects of single genes. However, both methods produce unbiased estimates of the marker gene effects. Data structure may influence results from these methods of analysis. For the least squares analysis, the percent variation ($R^2$) was also calculated.

Each set of litter records and ESR RFLP data were analyzed separately for each line. In the Line 94 data set, only the $F_1$ animals were used, since there were only a small group of $F_2$ animals.

Results

Using the two restriction endonucleases Pvu II and Pst I, a RFLP analysis was conducted for three lines of pigs (Line 02, Line 92, Line 94) from the Pig Improvement Company. Table 5 contains the summary of the results from the RFLP analysis with Line 92, Line 94, and Line 02 sows. The Line 94 females consisted of mostly $F_1$ animals, and these all had either the Pvu II 4.3 kb/4.3 kb genotype or the 3.7 kb/3.7 kb genotype. Only some of the $F_2$ animals (crosses of F1) had the Pvu II 3.7 kb/3.7 kb genotypes. The frequency of the ESR Pvu II and Pst I fragments in the PIC populations differed some from those seen in our U.S. pigs (Examples 1 and 2) and those in Meishan pigs (Example 2). This may represent changes in allelic frequency resulting from the genetic origin of the pigs in the PIC herds or from sampling.

Results of the analysis using the animal mixed model for Line 92 and Line 94 are found in Tables 6 and 7, respectively. For the Line 92 pigs, there is a 1.78 pig advantage in number born for females with the Pvu II 3.7 kb/3.7 kb genotype compared to the females with the Pvu II 4.3 kb/4.3 kb genotype. The females with the heterozygote genotype also had higher litter size than the females with the Pvu II 4.3 kb/4.3 kb genotype. Given the small sample size, the lack of a significant effect of the ESR Pvu II genotypes is not surprising. In the Line 94 females (Table 7) the difference in litter size between the genotypes is very small.

Results from the least squares analyses are in Tables 8 and 9. In both cases, there is clear evidence that the ESR Pvu II 3.7 kb fragment is closely associated with higher litter size. For the Line 92 females, those with the Pvu II 3.7 kb/3.7 kb genotypes had 3.25 more pigs born and 3.25 more pigs born alive than did the females with the Pvu II 4.3 kb/4.3 kb genotypes. Also, in the Line 94 females, those with the Pvu II 4.3 kb/3.7 kb genotype had 2.78 more pigs born in first litters (P<.06) and 3.51 more pigs born for all litters (P<.001) than did females with the Pvu II 4.3 kb/4.3 kb genotype. For the number of pigs born alive, similar large differences existed. The percent of variation explained by the ESR Pvu II genotypes was approximately 10% in the Line 92 females and ranged from 3% to 6% in the Line 94 pigs. These results clearly demonstrate that the ESR Pvu II 3.7 kb genotype is significantly associated with higher litter size in these lines of pigs.

Line 02 pigs all had the ESR Pvu II genotype 4.3 kb/4.3 kb, so no effect of the Pvu II fragments could be analyzed. For all three lines, analyses with the Pst I fragments failed to demonstrate a relationship between the ESR Pst I genotypes and litter size.

Discussion

Three important points need to be discussed. The first is why the ESR Pvu II 3.7 kb fragment is associated with higher litter size in the PIC lines when the ESR Pvu II 4.3 kb fragment was associated with higher litter size in the ISU Meishan herd. See Example 1. It is known that the Meishans at PIC and ISU were from separate importations and came from different breeding farms in China. These farms have been closed to outside animals for over 35 years. Therefore, since these animals represent two different populations of Meishans, it is likely that a recombination event has occurred between the Pvu II fragment and a beneficial litter size gene. See FIG. 2. Such an event would explain the apparent difference in the results. However these results clearly confirm that, depending on the population, the ESR Pvu II 4.3 kb fragment or its allele, the Pvu II 3.7 kb fragment, are associated with higher litter size.

The second point to note is the discrepancy in results between the least squares analysis and the animal mixed model methods in the Line 94 pigs. This may have been a function of the data structure, since on close examination the sib groups of females whose litter records and RFLP patterns were evaluated had limited within-family variation for the ESR genotypes. This may have caused some reduction in the effect of the ESR Pvu II genotype effect.

The final point is that, after looking at a number of polymorphic Pst I and Pvu II fragments, only the Pvu II 4.3 kb fragment and its allele, the 3.7 kb fragment, are associated with higher litter size. This suggests that they can be used in a marker assisted selection program to select for higher litter size. This would be accomplished by evaluating ESR Pvu II RFLP patterns in different populations and breeds and then selecting on either the Pvu II 4.3 kb or the 3.7 kb allele (depending on which is associated with the higher litter size in that population) to improve litter size.

Summary

Pigs from a population consisting of three lines of pigs from the Pig Improvement Company herds were analyzed to determine the relationship between restriction fragment length polymorphisms (RFLP) of the estrogen receptor gene (ESR) and litter size. DNA polymorphisms with Pst I and Pvu II restriction enzymes were observed and were included in two statistical methods of analysis to determine if they were associated with litter size. With both statistical methods, no Pst I fragments were related to higher litter size in any of the three lines evaluated from this data set. Using the animal mixed model approach, there was an association of the Pvu II 3.7 kb fragment with higher litter size in the Line 92 (Meishans) but not in the Line 94 (Meishan crossbred females). Using the least squares method of analysis, the Pvu II 3.7 kb fragment was significantly (P<.001) associated with higher litter size in the Line 94 animals, and there was an association of the Pvu II 3.7 kb fragment with higher litter size in the Line females. No relationship was seen with any Pvu II fragment and litter size in the Line 02 (primarily European Landrace) pigs. These results confirm previous data that the 3.7 kb Pvu II fragment or its allele (4.3 kb fragment) are associated with higher litter size in some breeds.

References

The following references are incorporated herein in their entirety:

Kennedy B. W., Quiton M. and van Avendonk J. A. M. (1992) Estimation of the effects of single genes on quantitative traits, *J. Animal Science* 70:2000-20012.

Rothschild M. F., Larson R. G., Jacobson C. and Pearson P. (1991) Pvu II polymorphisms at the porcine oestrogen receptor locus (ESR). *Animal Genetics* 22:448.

Rothschild M. F., Ruohonen-Lehto M. K., Larson R. G., Hergenrader C. J. and Tuggle C. K. (1992) Estrogen receptor gene restriction fragment length polymorphisms in U.S. breeds of swine. *J. Animal Science* 70 (suppl 1):41.

TABLE 4

Numbers of sows and litters.

| No. Sows | | | No. Litters | | |
|---|---|---|---|---|---|
| Line 92 | Line 94 | Line 02 | Line 92 | Line 94 | Line 02 |
| 21 | 105** | 62* | 21 | 188 | 196 |

*Only 49 animals with litter data
**Includes 17 $F_2$ animals also from this line

TABLE 5

Frequency of polymorphic Pvu II and Pst I fragments in PIC strains.

| Breed | No. of Animals | Polymorphic Fragments (kb) | | | | | | |
|---|---|---|---|---|---|---|---|---|
| | | Pvu II | | | Pst I | | | |
| | | 5.0 | 4.3 | 3.7 | 10.0 | 9.6 | 9.2 | 7.8 |
| PIC Line 92 | 21 | 0% | 81% | 71% | 0% | 100% | 100% | 33% |
| PIC Line 94* | 105 | 0% | 98% | 61% | 0% | 100% | 87% | 89% |
| PIC Line 02 | 62 | 0% | 100% | 0% | 84% | 76% | 6% | 96% |

*Includes $F_2$ animals

TABLE 6

Effect of ESR Pvu II genotype on number born (NB) and number born alive (NBA) in PIC Line 92 using animal mixed model analysis.*

| ESR Pvu II Genotype | NB | Overall Prob | NBA | Overall Prob |
|---|---|---|---|---|
| 4.3/4.3 | 11.06 | P < .32 | 10.57 | P < .30 |
| 4.3/3.7 | 12.48 | | 12.04 | |
| 3.7/3.7 | 12.84 | | 11.40 | |

*21 sows with first litter records only

TABLE 7

Effect of ESR Pvu II genotype on number born (NB) and number born alive (NBA) in PIC Line 94 using an animal mixed model analysis*

| Parity | ESR Pvu II Genotype | NB | Overall Prob | NBA | Overall Prob |
|---|---|---|---|---|---|
| 1st | 4.3/4.3 | 12.75 | P < .92 | 11.58 | P < .90 |

TABLE 7-continued

Effect of ESR Pvu II genotype on number born (NB) and number born alive (NBA) in PIC Line 94 using an animal mixed model analysis*

| Parity | ESR Pvu II Genotype | NB | Overall Prob | NBA | Overall Prob |
|---|---|---|---|---|---|
| | 4.3/3.7 | 12.77 | | 11.64 | |
| All | 4.3/4.3 | 12.88 | P < .88 | 12.19 | P < .90 |
| | 4.3/3.7 | 13.01 | | 12.29 | |

*87 first parity $F_1$ sows, 177 total records for all parities

TABLE 8

Effect of ESR Pvu II genotype on number born (NB) and number born alive (NBA) in PIC Line 92 using a least squares analysis*

| ESR Pvu II Genotype | NB | Overall Prob | Percent Variation Explained | NBA | Overall Prob | Percent Variation Explained |
|---|---|---|---|---|---|---|
| 4.3/4.3 | 10.00 | P < .43 | 10.9% | 9.36 | P < .48 | 10.1% |
| 4.3/3.7 | 12.75 | | | 12.11 | | |
| 3.7/3.7 | 13.25 | | | 12.61 | | |

*21 sows with first litter records only

TABLE 9

Effect of ESR Pvu II genotype on number born (NB) and number born alive (NBA) in PIC Line 94 using a least squares analysis*

| Parity | ESR Pvu II Genotype | NB | Overall Prob | Percent Variation Explained | NBA | Overall Prob | Percent Variation Explained |
|---|---|---|---|---|---|---|---|
| 1st | 4.3/4.3 | 11.01 | P < .06 | 4.1% | 10.46 | P < .10 | 3.0% |
| | 4.3/3.7 | 13.79 | | | 12.75 | | |
| All | 4.3/4.3 | 10.96 | P < .001 | 5.9% | 10.92 | P < .007 | 4.2% |
| | 4.3/3.7 | 14.47 | | | 13.88 | | |

*87 first parity $F_1$ sows, 177 total records for all parities

We claim:

1. A method of screening sows for determining which allele of a polymorphism is associated with the ability of a sow to produce above average litter size of a population in which the sow belongs comprising:
   (a) calculating the average or mean litter size for said population from the litter sizes of sows in said population;
   (b) digesting genomic DNA of each of said sows with a restriction enzyme that cuts at the same restriction site as Pvu II thereby generating a first restriction pattern;
   (c) separating the fragments obtained from said digestion;
   (d) detecting said fragments with a probe capable of hybridizing to said fragments so as to identify a polymorphism in the estrogen receptor gene;
   (e) said polymorphism being one identifiable by a 3.7 or 4.3 kilobase restriction fragment length polymorphism; and (f) correlating the polymorphism with the litter size to determine which of the two alleles is associated with above average litter size for the population.

2. The method of claim 1 wherein said restriction enzyme is Pvu II.

3. The method of claim 1 wherein said separation is by gel electrophoresis.

4. The method of claim 1 wherein said restriction enzyme is Pvu II and said RFLP is selected from the group consisting of a 3.7 Kb fragment and 4.3 Kb fragment.

5. The method of claim 1 wherein said group of sows are of breeds selected from the group consisting of Meishan, Fengjing, Minzhu, Duroc, Hampshire, Landrace, Large, White, Yorkshire, and Chester White and any crosses involving these breeds.

6. The method of claim 2 wherein said RFLP is a 4.3 kilobase fragment and is associated with increased litter size.

7. The method of claim 2 wherein said RFLP is a 3.7 kilobase fragment and is associated with increased litter size.

* * * * *